United States Patent [19]

Kuen

[11] Patent Number: 5,423,789

[45] Date of Patent: Jun. 13, 1995

[54] GARMENT WITH SELECTABLE FASTENERS

[75] Inventor: David A. Kuen, Neenah, Wis.

[73] Assignee: Kimberly-Clark Corporation, Neenah, Wis.

[21] Appl. No.: 40,953

[22] Filed: Mar. 31, 1993

[51] Int. Cl.$^6$ ............................................. A61F 13/15
[52] U.S. Cl. ..................................... 604/386; 604/391
[58] Field of Search ................................. 604/386–391

[56] References Cited

U.S. PATENT DOCUMENTS

| | | | |
|---|---|---|---|
| 1,245,655 | 11/1917 | Allen . | |
| 1,494,044 | 5/1924 | Ward et al. . | |
| 2,500,255 | 1/1947 | Lee | 128/284 |
| 2,516,951 | 4/1947 | Brink | 128/287 |
| 2,548,162 | 4/1951 | Karels | 128/284 |
| 2,564,094 | 5/1951 | Brandl | 128/284 |
| 2,566,139 | 4/1952 | Ostrovsky et al. | 128/284 |
| 2,827,052 | 3/1958 | Goodman et al. | 128/284 |
| 3,081,772 | 3/1963 | Brooks et al. | 128/287 |
| 3,094,990 | 4/1963 | Neilson | 128/289 |
| 3,110,312 | 11/1963 | Wirth | 128/287 |
| 3,141,461 | 7/1964 | Farris | 128/284 |
| 3,150,664 | 9/1964 | Noel | 128/287 |
| 3,196,511 | 7/1965 | Kintner | 24/204 |
| 3,359,980 | 12/1967 | Rosenblatt | 28/284 |
| 3,441,024 | 4/1969 | Ralph | 128/287 |
| 3,441,025 | 4/1969 | Ralph | 128/289 |
| 3,452,753 | 7/1969 | Sanford | 128/287 |
| 3,455,303 | 7/1969 | Wilson | 128/289 |
| 3,460,535 | 8/1969 | Behna | 128/288 |
| 3,530,859 | 9/1970 | Heimowitz | 128/284 |
| 3,618,608 | 11/1971 | Brink | 128/287 |
| 3,653,381 | 4/1972 | Warnken | 128/284 |
| 3,728,191 | 4/1973 | Wierzba et al. | 156/265 |
| 3,882,871 | 5/1975 | Taniguchi | 128/287 |
| 3,955,575 | 5/1976 | Okuda | 128/284 |
| 4,051,854 | 10/1977 | Aaron | 128/284 |
| 4,145,763 | 3/1979 | Abrams et al. | 2/403 |
| 4,171,239 | 10/1979 | Hirsch et al. | 156/461 |
| 4,241,462 | 12/1980 | Tagawa et al. | 2/406 |
| 4,259,957 | 4/1981 | Sonenstein et al. | 128/287 |
| 4,299,223 | 11/1981 | Cronkrite | 128/287 |
| B1 4,315,508 | 11/1981 | Bolick | 604/392 |
| 4,315,508 | 2/1982 | Bolick | 128/289 |
| 4,338,938 | 7/1982 | Seavitt | 128/284 |
| 4,340,563 | 7/1982 | Appel et al. | 264/518 |
| 4,388,075 | 6/1983 | Nesek et al. | 604/385 |
| 4,402,690 | 9/1983 | Redfern | 604/391 |
| 4,405,297 | 9/1983 | Appel et al. | 425/72 |
| 4,410,327 | 10/1983 | Baggaley | 604/391 |
| 4,445,242 | 5/1984 | Bowen | 5/484 |
| 4,475,912 | 10/1984 | Coates | 604/385 |
| 4,516,975 | 5/1985 | Mitchell | 604/385 A |
| 4,568,342 | 2/1986 | Davis | 604/391 |
| 4,578,072 | 3/1986 | Lancaster | 604/385 A |

(List continued on next page.)

FOREIGN PATENT DOCUMENTS 672690 7/1960 Canada .
0013463A1 7/1980 European Pat. Off. .

(List continued on next page.)

OTHER PUBLICATIONS

A 6-page document showing views from a product bag labeled "OSCO Extra Absorbency Belted Undergarments".

Two sample undergarments and one of each of the 2 types of straps accompanying the undergarments from the above-referenced product bag.

Primary Examiner—David J. Isabella
Assistant Examiner—Rob Clarke
Attorney, Agent, or Firm—Thomas M. Gage

[57] ABSTRACT

An absorbent garment includes a pair of strap members and a garment shell. Each strap member defines opposite first and second end regions, and each end region includes two different fasteners. For example, the different fasteners may be hook fasteners and buttons. The garment shell defines opposite first and second waist sections. A plurality of loop patches are attached to the garment shell. Each loop patch is desirably formed of a loop material that is adapted to releasably engage a hook fastener and include a button hole to receive a button. The wearer can select between either of the two different fasteners to attach the strap members to the garment shell.

3 Claims, 4 Drawing Sheets

U.S. PATENT DOCUMENTS

| | | | |
|---|---|---|---|
| 4,578,073 | 3/1986 | Dysart et al. | 604/397 |
| 4,589,878 | 5/1986 | Mitrani | 604/392 |
| 4,592,118 | 6/1986 | DeWoskin | 24/444 |
| 4,596,568 | 6/1986 | Flug | 604/369 |
| 4,597,760 | 7/1986 | Buell | 604/397 |
| 4,597,761 | 7/1986 | Buell | 604/397 |
| 4,610,680 | 9/1986 | LaFleur | 604/385 A |
| 4,610,682 | 9/1986 | Kopp | 604/385 R |
| 4,615,695 | 10/1986 | Cooper | 604/385 A |
| 4,617,022 | 10/1986 | Pigneul et al. | 604/391 |
| 4,623,339 | 11/1986 | Ciraldo et al. | 604/359 |
| 4,630,320 | 12/1986 | Van Gompel | 2/406 |
| 4,641,381 | 2/1987 | Heran et al. | 2/400 |
| 4,662,037 | 5/1987 | Provost et al. | 24/447 |
| 4,663,220 | 5/1987 | Wisneski et al. | 428/221 |
| 4,670,012 | 6/1987 | Johnson | 604/390 |
| 4,680,030 | 7/1987 | Coates et al. | 128/134 |
| 4,681,581 | 7/1987 | Coates | 604/391 |
| 4,704,117 | 11/1987 | Mitchell | 604/391 |
| 4,710,414 | 12/1987 | Northrup et al. | 428/43 |
| 4,728,326 | 3/1988 | Gilles | 604/391 |
| 4,745,926 | 5/1988 | Hlusko | 128/134 |
| 4,753,649 | 6/1988 | Pazdernik | 604/389 |
| 4,761,318 | 8/1988 | Ott et al. | 428/85 |
| 4,770,917 | 9/1988 | Tochacek et al. | 428/95 |
| 4,773,906 | 9/1988 | Krushel | 604/391 |
| 4,776,068 | 10/1988 | Smirlock et al. | 24/442 |
| 4,781,966 | 11/1988 | Taylor | 428/152 |
| 4,794,028 | 12/1988 | Fischer | 428/100 |
| 4,798,603 | 1/1989 | Meyer et al. | 604/378 |
| 4,801,298 | 1/1989 | Sorenson et al. | 604/384 |
| 4,834,742 | 5/1989 | Wilson et al. | 604/389 |
| 4,835,795 | 6/1989 | Lonon | 2/408 |
| 4,846,815 | 7/1989 | Scripps | 604/391 |
| 4,847,134 | 7/1989 | Fahrenkrug et al. | 428/138 |
| 4,854,136 | 8/1989 | Coslovi et al. | 66/191 |
| 4,869,724 | 9/1989 | Scripps | 604/389 |
| 4,870,725 | 10/1989 | Dubowik | 24/442 |
| 4,884,713 | 12/1989 | Handler | 220/23.4 |
| 4,886,512 | 12/1989 | Damico et al. | 609/385.2 |
| 4,887,338 | 12/1989 | Handler | 24/306 |
| 4,887,339 | 12/1989 | Bellanger | 24/575 |
| 4,891,868 | 1/1990 | Watanabe | 24/691 |
| 4,894,060 | 1/1990 | Nestegard | 604/391 |
| 4,908,025 | 3/1990 | Ketchum, Jr. | 604/327 |
| 4,909,802 | 3/1990 | Ahr et al. | 604/385.1 |
| 4,909,879 | 3/1990 | Ball | 156/164 |
| 4,923,456 | 5/1990 | Proxmire | 604/391 |
| 4,932,950 | 6/1990 | Johnson | 604/392 |
| 4,936,840 | 6/1990 | Proxmire | 604/385.2 |
| 4,937,887 | 7/1990 | Schreiner | 2/402 |
| 4,938,754 | 7/1990 | Mesek | 604/385 |
| 4,963,140 | 10/1990 | Robertson et al. | 604/389 |
| 4,964,860 | 10/1990 | Gipson et al. | 604/391 |
| 4,973,326 | 11/1990 | Wood et al. | 604/391 |
| 4,981,480 | 1/1991 | Gaudet et al. | 604/386 |
| 4,988,346 | 1/1991 | Pfefferkorn | 604/389 |
| 4,994,054 | 2/1991 | Pigneul et al. | 604/391 |
| 5,019,065 | 5/1991 | Scripps | 604/391 |
| 5,019,073 | 5/1991 | Roessler et al. | 604/391 |
| 5,021,111 | 6/1991 | Swenson | 156/264 |
| 5,026,450 | 6/1991 | Cucuzza et al. | 156/244.11 |
| 5,032,122 | 7/1991 | Noel et al. | 604/391 |
| 5,100,399 | 3/1992 | Janson et al. | 604/386 |
| 5,125,246 | 6/1992 | Shytles | 66/193 |
| 5,135,522 | 8/1992 | Fahrenkrug et al. | 604/385.1 |

FOREIGN PATENT DOCUMENTS

| | | |
|---|---|---|
| 0120790A1 | 10/1984 | European Pat. Off. |
| 0233364A2 | 8/1987 | European Pat. Off. |
| 0276890A2 | 8/1988 | European Pat. Off. |
| 0276970A2 | 8/1988 | European Pat. Off. |
| 0278866A1 | 8/1988 | European Pat. Off. |
| 0287388A2 | 10/1988 | European Pat. Off. |
| 0319249A1 | 6/1989 | European Pat. Off. |
| 0321232A1 | 6/1989 | European Pat. Off. |
| 0321234A1 | 6/1989 | European Pat. Off. |
| 0330793A1 | 9/1989 | European Pat. Off. |
| 0345014A3 | 12/1989 | European Pat. Off. |
| 0374730A2 | 6/1990 | European Pat. Off. |
| 2335165 | 8/1977 | France |
| 2586558A1 | 3/1987 | France |
| 63-2708 | 1/1988 | Japan |
| 493819 | 10/1938 | United Kingdom |
| 1428572 | 3/1976 | United Kingdom |
| 1430747 | 4/1976 | United Kingdom |
| 2074011 | 10/1981 | United Kingdom |
| 2144637 | 3/1985 | United Kingdom |
| 2200530 | 8/1988 | United Kingdom |
| 2201893 | 9/1988 | United Kingdom |
| 2233876 | 1/1991 | United Kingdom |
| 2242612 | 10/1991 | United Kingdom |
| 2248379 | 4/1992 | United Kingdom |
| WO85/03205 | 8/1985 | WIPO |
| WO88/06014 | 8/1988 | WIPO |
| WO88/07335 | 10/1988 | WIPO |
| WO91/03220 | 3/1991 | WIPO |
| WO91/08725 | 6/1991 | WIPO |
| WO92/10957 | 7/1992 | WIPO |

GARMENT WITH SELECTABLE FASTENERS

BACKGROUND OF THE INVENTION

The present invention relates generally to the field of garments with attachment systems. More particularly, the invention pertains to an improved absorbent garment that enables the wearer to select from more than one type of fastener for maintaining the garment in place.

The present invention is intended for use with a wide variety of garments that are to be worn in the crotch region. Such garments may include disposable absorbent articles, underwear, bathing suits, athletic supporters, prosthetics, or other personal care or health care garments. With particular reference to disposable absorbent articles, these articles include such things as incontinence garments, disposable diapers, briefs, training pants, or the like.

Garments of this type have generally included an attachment system for securing the garment in the crotch region of the wearer. Such attachment systems have routinely included a particular type of mechanical or adhesive fastener. Garment manufacturers have had to select a fastener that has the broadest appeal to its customers.

The individualized needs of consumers, on the other hand, give rise to a demand for more than one type of fastener. These needs may be based on factors such as impaired dexterity, design familiarity, discreetness under clothing, security of closure, or the like. Nonetheless, manufacturers have heretofore been unable to accommodate these varying fastener needs of consumers.

SUMMARY OF THE INVENTION

In response to the discussed inability of garment manufacturers to accommodate differing fastener preferences, a new attachment strap and garment have been discovered. An attachment strap according to the invention includes a strap member defining a first end region, an opposite second end region, and a central region therebetween. Each strap member includes a first fastener and a second fastener attached to the first end region. A garment according to this invention includes at least one of the foregoing strap members and a garment shell. The garment shell defines a first waist section, an opposite second waist section, and a crotch section therebetween. The garment shell includes a first retaining means located in the first waist section for releasably retaining the first fastener, and a second retaining means also located in the first waist section for releasably retaining the second fastener. The second end region of each strap member is attached to the second waist section of the garment shell.

This aspect of the invention allows the wearer of the garment to easily and conveniently select between two types of fasteners. In a preferred embodiment, the first fasteners are one element of hook-and-loop fasteners, such as hook fasteners, and the second fasteners are general fasteners, such as buttons.

In another preferred embodiment, an absorbent garment of the invention includes a pair of elastic strap members, with each strap member defining a first end region, an opposite second end region, and a central region therebetween. Each strap member includes a pair of hook fasteners, one attached to each end region. Each strap member also includes a pair of buttons, one attached to each end region. A garment shell defines a first waist section, an opposite second waist section, and a crotch section therebetween. The garment shell includes a liquid pervious bodyside liner, a substantially liquid impervious backing sheet attached to the bodyside liner, and an absorbent core sandwiched therebetween. A plurality of loop patches are attached to the backing sheet. Each loop patch is formed of a loop material adapted to releasably engage a hook fastener and define therein a button hole adapted to receive a button.

As set forth more fully below, each button is preferably located between a hook fastener and the central region of a strap member, and a bonded region is located between the hook fastener and the button. If the wearer elects to use the buttons, the wearer may optionally cut the strap member and remove the hook fasteners. Cutting through the bonded region minimizes raveling of the strap member.

Another aspect of the invention pertains to a method of using a garment of the foregoing type. The method includes selecting one of the different type of fasteners to use in attaching the strap members to the garment shell. This aspect gives the wearer a convenient option in selecting a fastener.

A still further aspect of the invention pertains to a method of making an absorbent garment. This method includes providing at least one strap member defining a first end region, an opposite second end region, and a central region therebetween; attaching a first fastener and a second fastener to the first end region of the strap member; providing a garment shell defining a first waist section, an opposite second waist section, and a crotch section therebetween; providing on the first waist section a first retaining member for releasably retaining the first fastener and a second retaining member for releasably retaining the second fastener; and providing means for attaching the second end region of the strap member to the second waist section of the garment shell.

As can be seen from the foregoing, the present invention accommodates the individualized fastener needs of consumers of absorbent garments.

Numerous other objects, features and advantages of the present invention will appear from the following description. In the description, reference is made to the accompanying drawings which illustrate a preferred embodiment of the invention. Such embodiment does not represent the full scope of the invention. Reference should therefore be made to the claims herein for interpreting the full scope of the invention.

DETAILED DESCRIPTION OF THE PREFERRED EMBODIMENT

Figure 1:
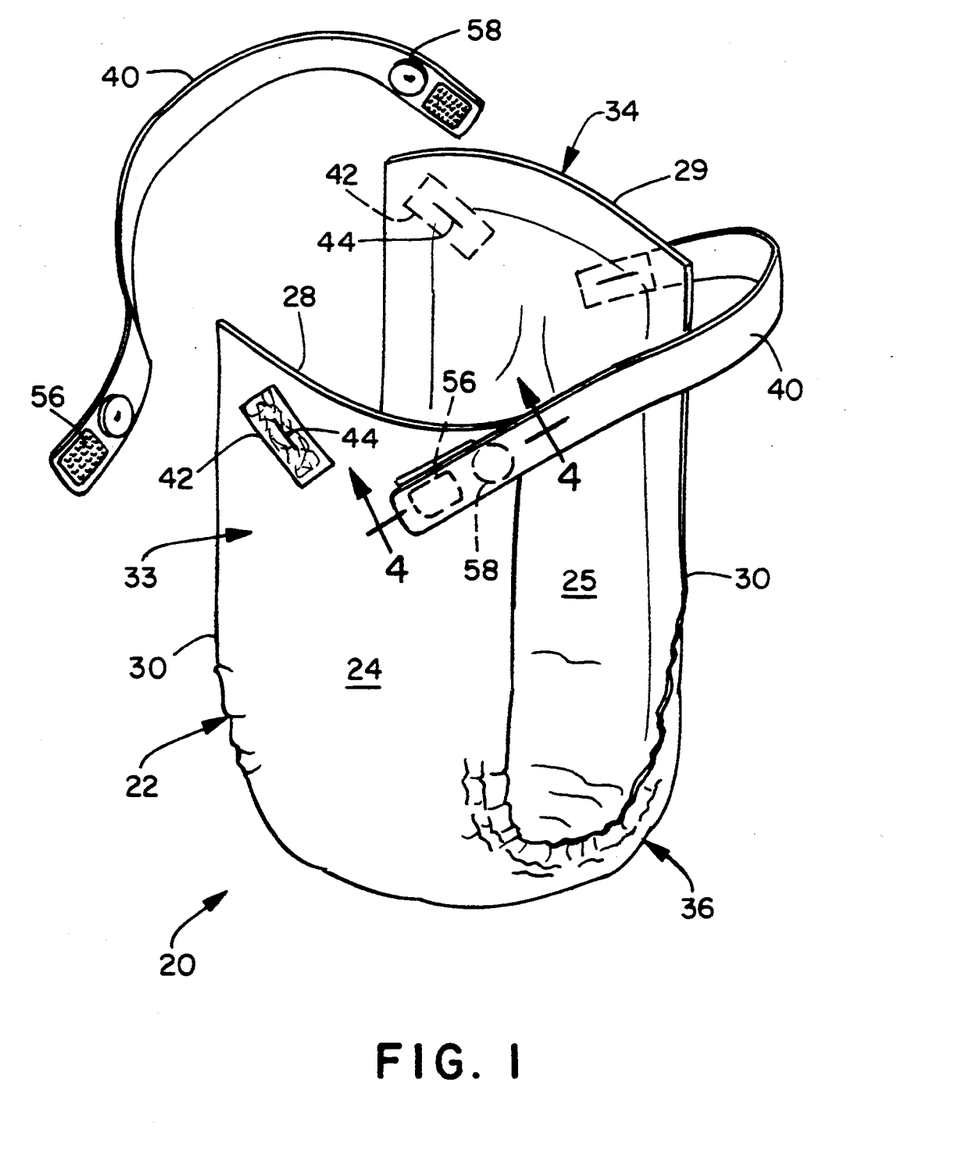
FIG. 1 is a partially-exploded perspective view of a disposable absorbent garment according to the present invention.
Figure 2:
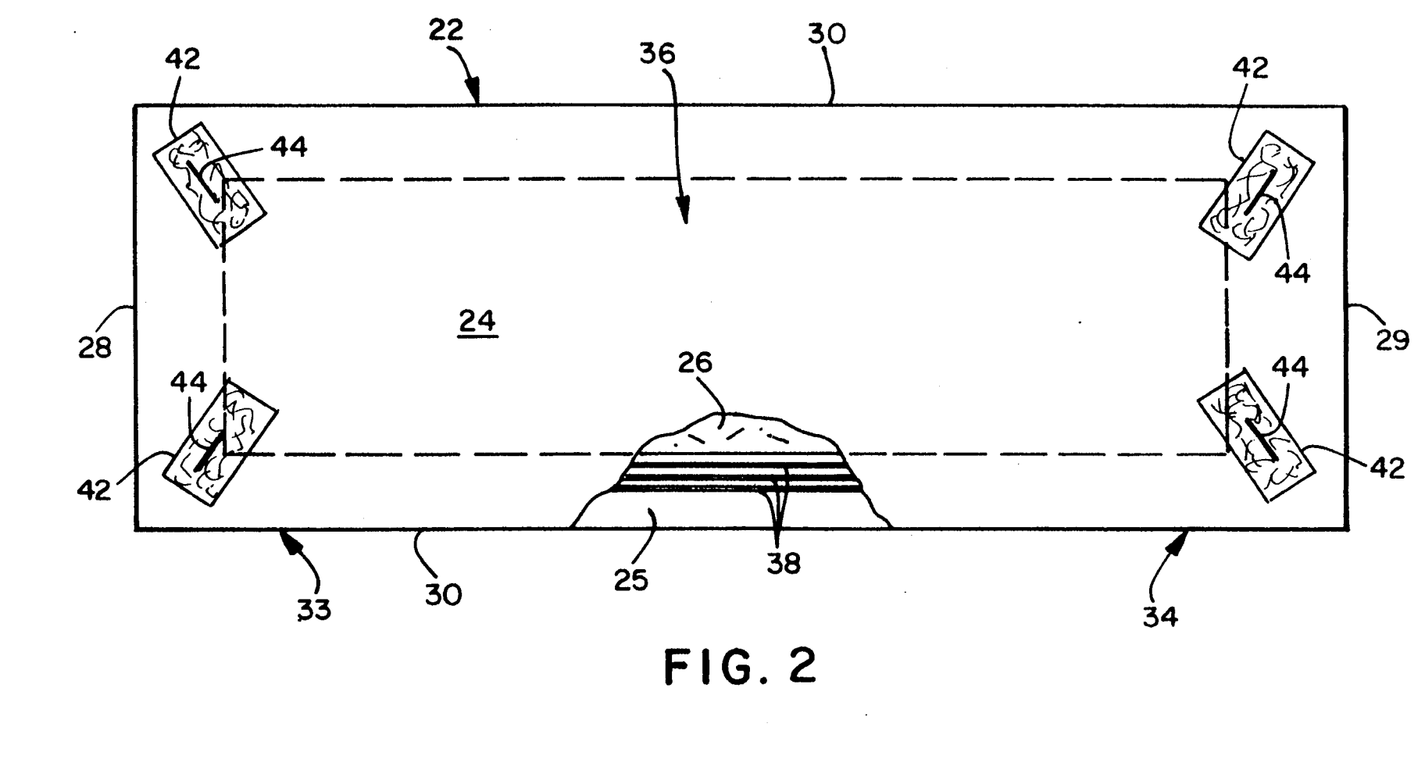
FIG. 2 is a plan view of a garment shell of the disposable absorbent garment shown in FIG. 1, with portions broken away for the purposes of illustration.

With reference to FIGS. 1 and 2, a disposable absorbent garment 20 formed according to the present invention is shown for purposes of illustration as an incontinence product for adults. The invention may also be embodied in other types of garments, such as other disposable absorbent articles, underwear, bathing suits, athletic supporters, prosthetics, or other personal care or health care garments.

The disposable absorbent garment 20 generally includes a garment shell 22 that is adapted to be used in conjunction with an attachment system. As shown, the shell 22 includes a substantially liquid impermeable backing sheet 24, a substantially liquid permeable bodyside liner 25, and an absorbent core 26 (FIG. 2) sandwiched between the backing sheet and the bodyside liner. The backing sheet 24 and bodyside liner 25 are preferably longer and wider than the absorbent core 26, so that the peripheries of the backing sheet and bodyside liner form margins which may be sealed together using ultrasonic bonds, thermal bonds, adhesives, or other suitable means. The absorbent core 26 may be attached to the backing sheet 24 and/or the bodyside liner 25 using ultrasonic bonds, adhesives, or other suitable means. The garment 20 may also include additional components to assist in the acquisition, distribution and storage of waste material. For example, the garment 20 may include a transport layer, such as described in U.S. Pat. No. 4,798,603 to Meyer et al., which is incorporated herein by reference to the extent that it is consistent herewith.

The garment shell 22 as shown is generally rectangular with a first or front end 28, an opposite second or back end 29, and longitudinal sides 30 extending between the first and second ends. The garment shell 22 defines a first or front waist section 33 adjacent the first end 28 and an opposite second or back waist section 34 adjacent the second end 29. A crotch section 36 is located intermediate the first and second waist sections 33 and 34. When the garment shell 22 is placed on a wearer, the first waist section 33 is generally the portion of the garment located forward of the crotch region of the wearer, and the second waist section is generally the portion of the garment located rearward of the crotch region of the wearer. The garment shell 22 may be rectangular with a length in the range of from about 10 to about 34 inches (ca. 25–86 cm.), and a width in the range of from about 2 to about 22 inches (ca. 5–56 cm.). Of course, the garment shell 22 may optionally be T-shaped, I-shaped, hourglass-shaped, or irregularly-shaped.

The shell 22 may include elastic strands or ribbons 38 (FIG. 2) longitudinally orientated along each side margin of the garment 20 and attached in a stretched condition to the backing sheet 24, the liner 25, or both. The elastic strands 38 are located in the crotch section 36 and extend toward or into the first and second waist sections 33 and 34. The elastic strands 38 may assist in holding the shell 22 against the body of the wearer or forming seals or gaskets about the leg of the wearer.

The attachment system in the illustrated embodiment of the invention includes a pair of strap members 40 and four retaining members. The retaining members are adapted to releasably engage the different fasteners on the strap members 40. As illustrated, the retaining members are in the form of four loop patches 42 which comprise the loop component of a hook-and-loop fastening system. The loop patches may be identical in shape and formed of any suitable loop material. The term loop material is intended, in one embodiment, to mean a structure having a base portion and a plurality of loop members extending upwardly from at least one surface of the base portion. The loop material can comprise a fabric material manufactured to have a raised loop construction, stabilized through napping and thermosetting so that the individual loops are erect from the fabric base. The loop material may be formed of any suitable material, such as acrylic, nylon, polypropylene or polyester, and may be formed by methods such as warp knitting, stitch bonding, extruding or needle punching. The loop patches 42 can also be any suitable material having non-woven loops, with or without a base portion.

In a preferred embodiment, the loop patches 42 have a two bar warp knit construction, with from 21 to 41 courses per inch (ca. 8–16 per cm.) and from 26 to 46 wales per inch (ca. 10–18 per cm.), of polyester yarn. In particular, about 15–35 percent of the yarns may be composed of yarn having about 1–30 individual filaments therein and having a yarn denier within the range of about 15–30 d (denier). In addition, about 65–85 percent of the yarns may be composed of yarn having about 1–30 individual filaments therein and having a yarn denier within the range of about 20–55 d. Also, the loops may particularly be formed with a loop height from about 2 to about 2.5 millimeters. The caliper may be from about 0.010 to about 0.040 inch (ca. 0.25–1 mm.) and the basis weight may be from about 1.0 to about 3.0 ounces per square yard (ca. 34–102 grams per square meter). One particular material which has been found suitable for the loop patches 42 is identified as No. 19902 and is available from Guilford Mills of Greensboro, N.C., U.S.A.

The loop patches 42 are located in the first and second waist sections 33 and 34 and are attached to the surface of the backing sheet 24 that is remote from the bodyside liner 25. The two loop patches 42 in the first waist section 33 are preferably separated from one another and spaced from the first end 28 and the longitudinal sides 30 by at least about 0.25 inch (ca. 6.5 mm.). Correspondingly, the two loop patches 42 in the second waist section 34 are preferably separated from one another and spaced from both the second end 29 and the longitudinal sides 30 by at least about 0.25 inch (ca. 6.5 mm.).

Each loop patch 42 is preferably formed with and defines therein a buttonhole 44 (see FIG. 2). Each buttonhole 44 represents a cut, slit, punch hole or other suitable opening in the loop material. Preferably, the buttonhole 44 extends completely through the loop material, backing sheet 24, and bodyside liner 26. The buttonholes 44 are desirably but not necessarily formed at locations which avoid the absorbent core 26.

The geometric shape of the loop patches 42 may take any form, such as square, rectangular, irregular, oval, round, etc. The size of the loop patches 42 should be sufficient to be readily detectible by sight and touch and accommodate the buttonhole 44. Desirably, each loop patch is rectangular in shape measuring about 4 inches by about 1.25 inches (ca. 10 by 3 cm.). Each buttonhole 44 is desirably centered on a loop patch 42 and aligned with its long dimension.

The loop patches 42 are attached by ultrasonic bonds, thermal bonds, stitching, adhesives, or other suitable means, so that the loops of the loop material extend outwardly from the backing sheet 24. The loop patches 42 are desirably attached as illustrated in FIG. 2, such that the long dimension of each loop patch forms an angle of about 35 degrees with the transverse axis of the garment shell 22. Alternately, the loop patches may be attached at angles with respect to the longitudinal axis of the garment using a plurality of lines of adhesive (not shown), as disclosed in commonly assigned U.S. patent application Ser. No. 07/998,496 filed Dec. 30, 1992, by D. A. Kuen et al. for a "Garment Attachment System". Still alternately, the loop patches 42 may be aligned with the longitudinal or transverse axes of the garment shell 22 (not shown).

Figure 6:
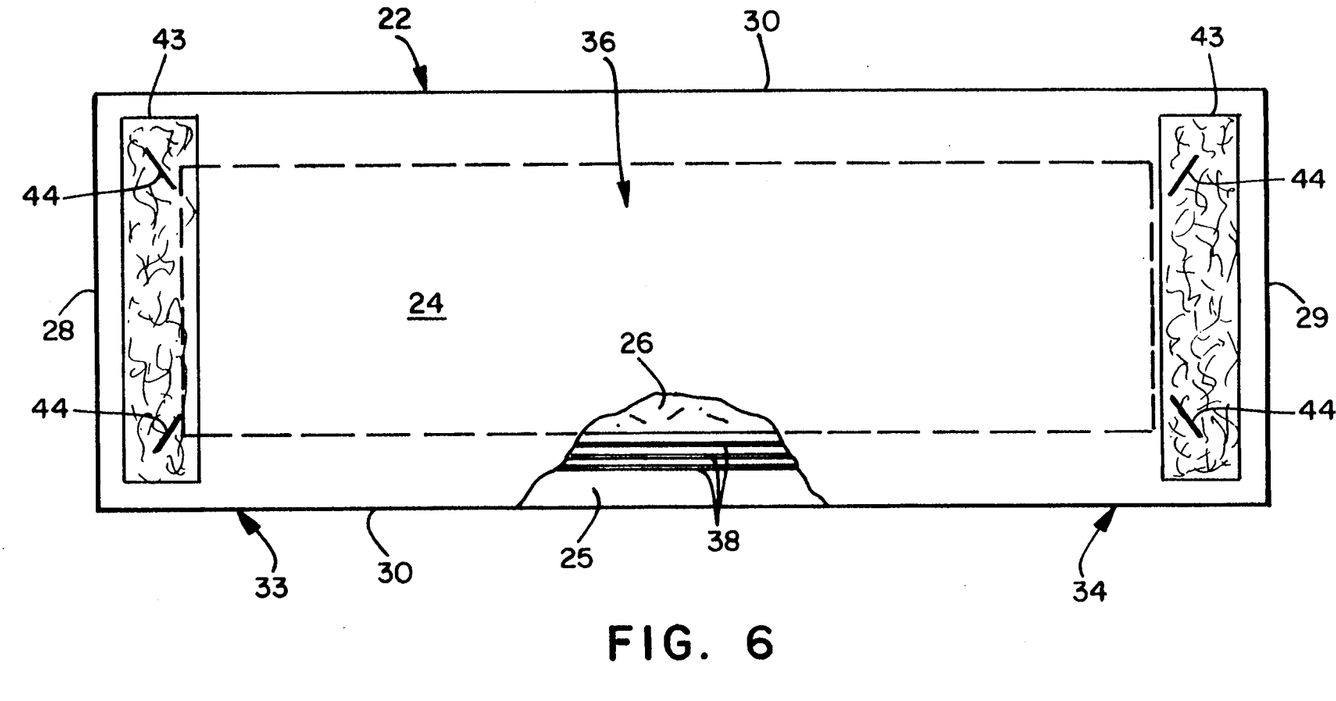
FIG. 6 is a plan view similar to FIG. 2, but showing an alternate embodiment of a garment shell of the inven-

As an alternative to using four loop patches 42, the attachment system could be constructed with a loop patch (not shown) that covers or is located in at least portions of both the first and second waist sections 33 and 34. Such a single patch of loop material could be attached to or formed integrally with the backing sheet 24. Still optionally, the attachment system could be constructed with a pair of loop patches 43 (see FIG. 6), one located in and extending transversely across the first waist section 33 and one located in and extending transversely across the second waist section 34. In either option, two, four or more buttonholes 44 could be formed through the loop material. It should also be understood that the buttonholes 44 may be formed in the garment shell 22 separate from the loop patches 42. In this instance, the retaining member would comprise the loop patches and the portion of the garment shell defining the buttonholes.

Figure 3:
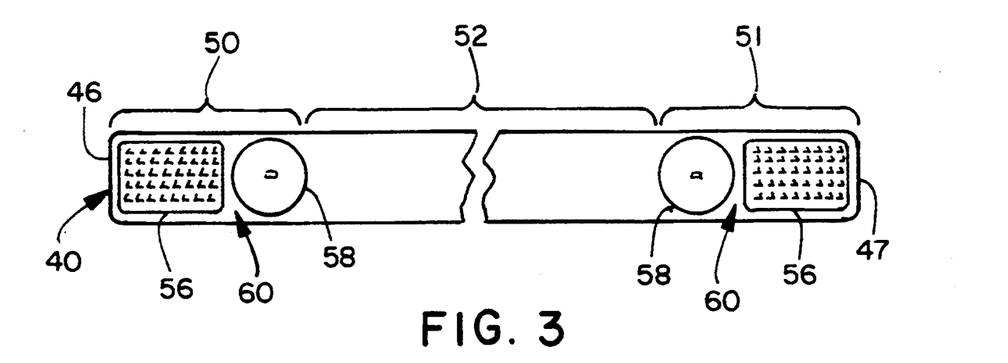
FIG. 3 is an enlarged plan view of a strap member of the disposable absorbent garment shown in FIG. 1.
Figure 4:
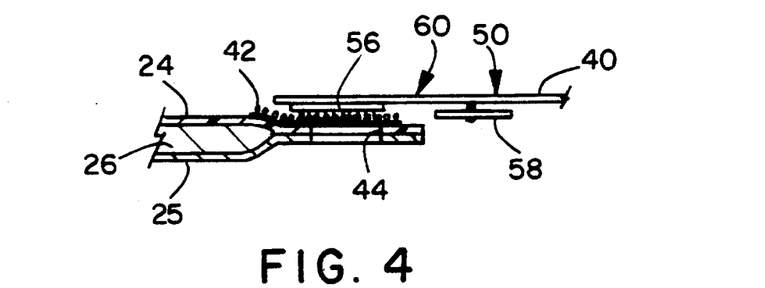
FIG. 4 is an enlarged view in section taken generally from the plane of the line 4—4 in FIG. 1.

With additional reference to FIGS. 3 and 4, the strap members 40 are each generally rectangular strips of material having opposite first and second ends 46 and 47. Each strap member 40 defines a first end region 50 extending inward from the first end 46, an opposite second end region 51 extending inward from the second end 47, and a central region 52 between the end regions 50 and 51. The end regions 50 and 51 define the portions of a strap member 40 where fasteners are attached to secure the strap member to the first and second waist sections 33 and 34. The central region 52 represents the portion of the strap member 40 generally positioned against a hip of the wearer when the garment 20 is worn.

The strap members 40 are preferably formed of an elastic material, which is capable of stretching to approximately 2.8 to 3 times its relaxed length. The strap members 40 preferably have a relaxed length from about 6 inches to about 16 inches (ca. 15–41 cm.), and a width from about 0.5 inch to about 1.5 inches (ca. 1–4 cm.). For example, each strap member 40 may be 13.5 inches (ca. 34 cm.) long and 1 inch (ca. 2.5 cm.) wide. The ends of the strap members 40 may be bonded by ultrasonics, adhesives or other suitable means to prevent raveling. Alternately, only the central region 52 could be formed of an elastic material.

Both a first fastener 56 and a second fastener 58 are attached to the first end region 50 of each strap member 40. The fasteners 56 and 58 are different types of fasteners so that the wearer of the garment 20 can select the type of fastener that is most preferred. As illustrated, the first fastener 56 is a hook fastener and forms the hook component of a hook-and-loop fastener.

The second fastener 58 is of a type herein referred to as a general fastener, and in particular is a button held in place with an attachment thread. The term "general fastener" is used herein to encompass fasteners such as buttons, snap fasteners, clips, or the like fasteners having an enlarged head that is releasably retained in a slot or aperture, such as the arrowhead fastener disclosed in U.S. Pat. No. 4,315,508 issued Feb. 16, 1982, to Bolick, which is incorporated herein by reference to the extent that it is consistent herewith. The term "general fastener" also includes adhesive or tape fasteners, or string ties, but does not include hook-and-loop fasteners.

A hook fastener 56 and a button fastener 58 are also attached to the second end region 51 of each strap member 40. Alternately, other suitable means could be employed for attaching the second end region 51 of each strap member 40 to the second waist section 34 of the garment shell 22. For example, the second end region 51 could be attached to the second waist section 34 by a permanent thermal, adhesive, ultrasonic or sewn bond, or releasably attached using only a single type of fastener and corresponding retaining member.

As illustrated in FIGS. 1 and 3, the hook fasteners 56 and the buttons 58 are all attached on the same main planar surface of the strap member 40. Further, at each end region 50 and 51, the button 58 is desirably located between the hook fastener 56 and the central region 52. Each end region 50 and 51 may also include a bonded region 60 between the hook fastener 56 and the button 58. The bonded region 60 represents an area of the strap member 40 that has been treated so that it resists raveling if the strap member is cut in that area. Suitable treatment for the bonded region 60 may include ultrasonic bonding, adhesive application, thermal treatment, pressure application, or the like.

The hook fasteners 56 comprise a single-sided hook material. The hook fasteners 56 may be of a variety of shapes, such as rectangular and measuring about 0.875 inch by about 1.125 inches (ca. 2.2 by 2.9 cm.). Each hook fastener is attached to a strap member 40 by ultrasonic bonds, thermal bonds, adhesives, stitches or other suitable means. As illustrated in FIGS. 1 and 3, each hook fastener 56 has hooks extending to the periphery of the fastener, and is positioned in full face-to-face contact with the strap members 40. Alternately, the hook fasteners 56 may be positioned such that hook fasteners extend past the ends of the strap members, and include edge portions that are void of hooks (not shown).

Suitable hook material may be molded or extruded of nylon, polypropylene or another suitable material. Desirable stiffness levels of the hook material may be obtained from polymeric materials having a flexural modulus of about 70,000–120,000 pounds per square inch (ca. $4.83 \times 10^8 - 8.27 \times 10^8$ nt/m$^2$) and a Shore hardness value within the range of about D-40 to D-80, such as D-61. The hook fasteners 56 desirably contain uni-directional hooks, with the machine direction of the hooks aligned with the longitudinal axis of the strap member 40, and the hooks facing toward the opposite end portion 46 or 47 of the strap member. One suitable single-sided hook material for the hook fasteners is available from Velcro Industries B. V., Amsterdam, Netherlands or affiliates thereof, and is identified as HTH 708 with No. 22 uni-directional hook pattern. Other suitable hook materials would include woven materials with cut monofilaments forming hooks.

The shape, density and polymer composition of the hooks may be selected to obtain desirable peel and shear force resistance values between the hook fasteners 56 and the loop patches 42. For instance, a more aggressive hook material may comprise a material with a greater average hook height, a greater percentage of directionally-aligned hooks, or a more aggressive hook shape. As one example, the density of the hook members may be more than 50 hooks per square inch (ca. 8 per square cm.), and more particularly within the range of about 440 to about 1040 hooks per square inch (ca. 68-161 per square cm.), such as about 740 hooks per square inch (ca. 115 per square cm.). The row density may be within the range of about 20 to about 60 rows per linear inch of width (ca. 8-24 per linear cm.), such as about 40 rows per linear inch of width (ca. 16 per linear cm.). The hook members may be hook-shaped, mushroom-shaped, arrow-shaped or any other desired shape.

In use, the garment shell 22 is positioned on the body of the wearer and secured in position using the attachment system. The first or front waist section 33 is located toward the front of the wearer, the second or back waist section 34 is located toward the posterior of the wearer, and the crotch section 36 is in place to receive body exudate. The wearer then selects which of the first or second fasteners 56 or 58 is best suited to the wearer's needs. If the hook fastener 56 is selected, the wearer can engage the hook fastener on the first end region 50 to the loop patch 42 on the first waist section 33, and engage the hook fastener on the second end region 51 to the loop patch on the second waist section 34. This hook-and-loop attachment is illustrated in FIGS. 1 and 4. The hook fasteners 56 can be readily removed by pulling on a portion of each strap member near a hook fastener 56 to release the hook-and-loop engagement.

Figure 5:
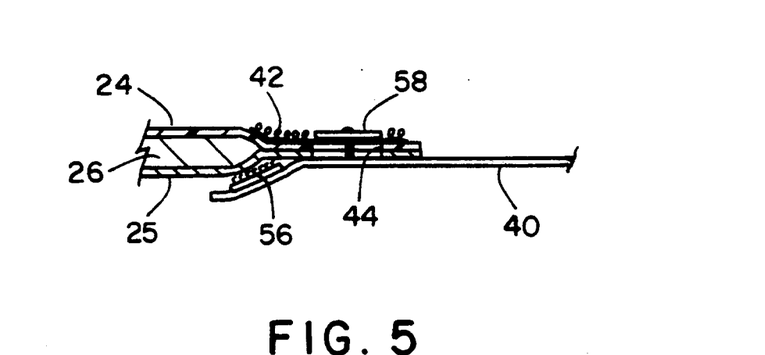
FIG. 5 is an enlarged view in section similar to FIG. 4, but showing a strap member being attached to the garment shell using a button.

Alternately of course, the wearer can opt to use the buttons 58, as illustrated in FIG. 5. The wearer would then insert the button 58 in the second end region 51 of each strap member 40 through the buttonholes 44 on the second waist section 34, and insert the button in the first end region 50 of each strap member through the buttonholes on the first waist section 33. As shown in FIG. 5, the button 58 is preferably inserted through the buttonholes 44 from the bodyside to the backing sheet side. The button 58 is thus positioned away from the wearer, and the hook fastener 56 rests against the bodyside liner. By forming the buttonholes 44 in the loop patches 42, rather than separately therefrom, the loop material reinforces the buttonholes and reduces the likelihood that the button 58 will tear the garment shell 22.

The loop patches 42 with buttonholes 44 formed therein function as retaining members to releasably engage both the first fasteners 56 and the second fasteners 58. If fasteners other than the illustrated hook fastener 56 and button 58 are used on the strap member 40, a retaining member other than the combined loop material and buttonhole may be required to provide the desired releasable engagement. For example, the retaining member may comprise a specially sized or shaped aperture to receive the fastener, a mating clip or snap, a frictionally-enhanced woven or nonwoven material, a region providing adhesive properties, or the like.

Should the wearer decide to use the second fasteners 58 for all future uses, the wearer can cut the strap members 40 to permanently remove the first fasteners 56. Preferably, the strap members 40 are cut through the bonded region 60 so that raveling of the straps will be kept to a minimum. On the other hand, the wearer could permanently remove the second fasteners 58 by cutting their attachment threads in the case of buttons. Although removing unused fasteners 56 or 58 may reduce the potential for skin irritation, both fasteners can be kept on the strap members 40.

A wide variety of materials may be used to construct the aforementioned components of the garment 20. The backing sheet 24, for example, may comprise a thin, substantially liquid impermeable web or sheet of plastic film such as polyethylene, polypropylene, polyvinyl chloride or similar material. The backing sheet material may be transparent or opaque and have an embossed or matte surface. One preferred material for the backing sheet 24 is a polyethylene film that has a nominal thickness of about 0.001 inch and a systematic matte embossed pattern, and that has been corona treated on both sides. Alternately, the backing sheet 24 may comprise a nonwoven, fibrous web which has been suitably constructed and arranged to be substantially liquid impermeable. Still alternately, the backing sheet may comprise a layered or laminated material, such as a thermally bonded plastic film and nonwoven web composite.

The bodyside liner 25 may be any soft, flexible, porous sheet which passes fluids therethrough. The bodyside liner 25 may comprise, for example, a nonwoven web or sheet of wet strength tissue paper, a spunbonded, meltblown or bonded-carded web composed of synthetic polymer filaments, such as polypropylene, polyethylene, polyesters or the like, or a web of natural polymer filaments such as rayon or cotton. The bodyside liner 25 has a pore size that readily allows the passage therethrough of liquids, such as urine and other body exudates. The liner 25 may be selectively embossed or perforated with discrete slits or holes extending therethrough. Optionally, the web or sheet may be treated with a surfactant to aid in liquid transfer. One preferred bodyside liner material is a wettable spunbonded polypropylene having a basis weight of 0.7 ounces per square yard. Such material may be produced by the methods and apparatus described in U.S. Pat. Nos. 4,340,563 and 4,405,297 to Appel et al., which are incorporated herein by reference.

The absorbent core 26 is preferably an air-formed batt of cellulosic fibers (i.e., wood pulp fluff). One preferred type of wood pulp fluff, which is available under the trade designation CR1654 from Kimberly-Clark Corporation of Neenah, Wis., U.S.A., is a bleached, highly absorbent sulphate wood pulp containing softwood fibers. Optionally, the absorbent core 26 could comprise a coform material composed of a mixture of cellulosic fibers and synthetic polymer fibers. For example, the coform material may comprise an airlaid blend of cellulosic wood fibers and meltblown polyolefin fibers, such as polyethylene or polypropylene fibers.

The absorbent core 26 may also include compounds to increase its absorbency, such as an effective amount of organic or inorganic high-absorbency materials. For example, the absorbent core 26 can include 0-95 weight percent high-absorbency material. Suitable inorganic high-absorbency materials include, for example, absorbent clays and silica gels. Organic high-absorbency materials can include natural materials, such as pectin, guar gum and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine or the like. Other suitable polymers can include hydrolyzed acrylonitrile grafted starch, acrylic acid grafted starch, and isobutylene maleic anhydride copolymers, and mixtures thereof. The hydrogel polymers are preferably sufficiently cross-linked to render the materials substantially water-insoluble. Cross-linking may, for example, be by irradiation or by covalent, ionic, van der Waals, or hydrogen bonding. Suitable materials are available from various commercial vendors, such as Dow Chemical Company, Hoechst-Celanese Corporation, and Allied-Colloid. Typically, the high-absorbency material is capable of absorbing at least about 15 times its weight in water, and preferably is capable of absorbing more than about 25 times its weight in water.

The high-absorbency material can be distributed or otherwise incorporated into the absorbent core 26 employing various techniques. For example, the high-absorbency material can be substantially uniformly distributed among the fibers comprising the absorbent core. The materials can also be nonuniformly distributed within the absorbent core fibers to form a generally continuous gradient with either an increasing or decreasing concentration of high-absorbency material, as determined by observing the concentration moving inward from the backing sheet 24. Alternatively, the high-absorbency material can comprise a discrete layer separate from the fibrous material of the absorbent core 26, or can comprise a discrete layer integral with the absorbent core.

The absorbent core 26 may also include a tissue wrap layer to help maintain the integrity of the fibrous core. This tissue wrap typically comprises a hydrophilic cellulosic material, such as creped wadding or a high wet-strength tissue.

The elastic strands 38 may be formed of a dry-spun coalesced multifilament elastomeric thread sold under the tradename LYCRA and available from I.E. Du Pont de Nemours and Company. Alternately, the leg elastic members 38 may be formed of other typical elastics utilized in the diaper-making art, such as a thin ribbon of natural rubber. Elasticity could also be imparted to the longitudinal side sections by extruding a hot melt elastomeric adhesive between the backing sheet 24 and the bodyside liner 25. Other suitable elastic gathering means are disclosed in U.S. Pat. Nos. 4,938,754 to Mesek and 4,388,075 to Mesek et al.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, the components of the fasteners 56 and 58 may be reversed. For example, the hook material may be located on the garment shell 22 and the loop material may be located on the strap members 40. Also, the first and second fasteners 56 and 58 may be attached on opposite main surfaces of the strap members 40, and the terms first end region and second end region do not necessarily correspond exclusively to a front or back end. Likewise, the attachment system may be associated with garments other than the disposable absorbent garments as described herein. Therefore, the invention should not be limited by the specific embodiments described, but only by the claims.

I claim:

1. A garment comprising:
   a pair of strap members, each strap member defining a first end region, an opposite second end region, and a central region between the first and second end regions, each strap member comprising:
   a pair of hook fasteners, one hook fastener being attached to the first end region and one hook fastener being attached to the second end region; and
   a pair of buttons, one button being attached to the first end region and one button being attached to the second end region, each of the buttons being located between one of the hook fasteners and the central region of the strap member; and
   a garment shell defining a first waist section, an opposite second waist section, and a crotch section between the first and second waist sections, the garment shell comprising retaining means for releasably retaining the hook fasteners and the buttons, the retaining means being located in the first waist section and located in the second waist section, the retaining means comprising a loop material and defining therein button holes.

2. A garment comprising:
   a pair of strap members, each strap member defining a first end region, an opposite second end region, and a central region between the first and second end regions, each strap member comprising:
   a pair of hook fasteners, one hook fastener being attached to the first end region and one hook fastener being attached to the second end region; and
   a pair of buttons, one button being attached to the first end region at a location between one of the hook fasteners and the central region, one button being attached to the second end region at a location between one of the hook fasteners and the central region, the first and second end regions of each of the strap members further including a bonded region located between the hook fastener and the button; and
   a garment shell defining a first waist section, an opposite second waist section, and a crotch section between the first and second waist sections, the garment shell comprising retaining means for releasably retaining the hook fasteners and the buttons, the retaining means being located in the first waist section and located in the second waist section, the retaining means comprising a loop material and defining therein button holes.

3. An absorbent garment comprising:
   a pair of elastic strap members, each strap member defining a first end region, an opposite second end region, and a central region between the first and second end regions, each strap member comprising:
   a pair of hook fasteners, one hook fastener being attached to the first end region and one hook fastener being attached to the second end region; and
   a pair of buttons, one button being attached to the first end region and one button being attached to the second end region, each of the buttons being located between one of the hook fasteners and the central region of a strap member; and a garment shell defining a first waist section, an opposite second waist section, and a crotch section between the first and second waist sections, the garment shell comprising a plurality of loop patches formed of a loop material adapted to releasably engage the hook fasteners, each of the loop patches defining therein a button hole adapted to receive one of the buttons.

* * * * *